United States Patent [19]
Grose

[11] Patent Number: 5,710,248
[45] Date of Patent: Jan. 20, 1998

[54] PEPTIDE TAG FOR IMMUNODETECTION AND IMMUNOPURIFICATION

[75] Inventor: Charles F. Grose, Iowa City, Iowa

[73] Assignee: University of Iowa Research Foundation, Iowa City, Iowa

[21] Appl. No.: 681,935

[22] Filed: Jul. 29, 1996

[51] Int. Cl.$^6$ .............. A61K 38/04; C07K 1/00; C07K 5/00; G01N 33/53
[52] U.S. Cl. .............. 530/327; 530/402; 530/403; 435/7.1; 435/7.7; 435/7.9
[58] Field of Search .............. 530/300, 327, 530/402, 350, 403; 435/7.1, 7.7, 7.9

[56] References Cited

U.S. PATENT DOCUMENTS

| 4,812,559 | 3/1989 | Ellis et al. | 536/27 |
|---|---|---|---|
| 4,950,595 | 8/1990 | Masuho et al. | 530/387 |
| 4,952,674 | 8/1990 | Keller et al. | 530/326 |

FOREIGN PATENT DOCUMENTS

| 0 321 249 A2 | 6/1989 | European Pat. Off. | |
| 0 482 671 A1 | 4/1992 | European Pat. Off. | |
| WO 95/04080 | 2/1995 | WIPO | |
| WO9601900 | 5/1996 | WIPO | C12N 15/38 |

OTHER PUBLICATIONS

B.L. Brizzard et al., "Immunoaffinity Purification of FLAG® Epitope-Tagged Bacterial Alkaline Phosphatase Using a Novel Monoclonal Antibody and Peptide Elution", Bio Techniques 16 730-735 (1994).
A.J. Davison et al., "The Complete DNA Sequence of Varicella-Zoster Virus", J. Gen. Virol., 67 1759-1816 (1986).
K.M. Duus et al., "Cell Surface Expression and Fusion by the Varicella-Zoster Virus gH:gL Glycoprotein Complex: Anlaysis by Laser Scanning Confocal Microscopy", Virology, 210 429-440 (1995).
B. Forghani et al., "Epitopes Functional in Neutralization of Varicella-Zoster Virus", J. Clin. Microbiology, 28 2500-2506 (1990).
Fowler et al., "Identification of Immunodominant Regions and Linear B Cell Epitopes of the gE Envelope Protein of Varicella-Zoster Virus", Virology, 214 531-540 (1995).
W. E. Friedrichs et al., "Glycoprotein gp118 of Varicella-Zoster Virus: Purification by Serial Affinity Chromatography", J. of Virology, 49 992-996 (1984).
J.E. Fulton et al., "Functional analysis of avian class I (BFIV) glycoproteins by epitope tagging and mutagenesis in viro" Eur. J. Immunol., 25 2069-2076 (1995).
C. Grose, "Glycoproteins Encoded by Varicella-Zoster Virus: Biosynthesis, Phosphorylation, and Intracellular Trafficking", Annu. Rev. Microbiol., 44 59-80 (1990).

C. Grose et al., "Monoclonal Antibodies Against Three Major Glycoproteins of Varicella-Zoster Virus", Infect. Immun., 40 381-388 (1983).
D.H. Jones et al., "A Rapid Method for Recombination and Site-Specific Mutagenesis by Placing Homologous Ends on DNA Using Polymerase Chain Reaction", Bio Techniques, 10 62-66 (1991).
P. Keller et al., "Identification and Sequence of the Gene Encoding gpIII, a Major Glycoprotein of Varicella-Zoster Virus", Virology, 157 526-533 (1987).
E.A. Montalvo et al., "Neutralization Epitope of Varicella Zoster Virus on Native Viral Glycoprotein gp118 (VZV Glycoprotein gpIII)", Virology, 149 230-241 (1986).
E.A. Montalvo et al., "Structural Analysis of the Varicella-Zoster Virus gp98-gp62 Complex: Posttranslational Addition of N-Linked and O-Linked Oligosaccharide Moieties", J. Virol. 53 761-770 (1985).
Z. Olah et al., "A Cloning and ε-Epitope-Tagging Insert for the Expression of Polymerase Chain Reaction-Generated cDNA Fragments in Escherichia coli and Mammalian Cells", Anal. Biochem., 221 94-102 (1994).
K.S. Prickett et al., "A Calcium-Dependent Antibody for Identification and Purification of Recombinant Proteins", Bio Techniques 7 580-589 (1989).
A. Vafai, "Antibody-binding sites on truncated forms of varicella-zoster virus gpI(ge) glycoprotein", Vaccine, 12(4) 1265-1269 (1994).
A. Vafai et al, "Existence of similar antigenic-sites on varicella-zoster virus gpI and gpIV", Virus Res., 13 319-336 (1989).
A. Vafai, et al., "Recognition of Similar Epitopes on Varicella-Zoster Virus gpI and gpIV by Monoclonal Antibodies", J. of Virology, 62 2544-2551 (1988).
P. Walter et al., "Signal Sequence Recognition and Protein Targeting to the Endoplasmic Reticulum Membrane", Annu. Rev. Cell. Biol., 10 87-119 (1994).
Z. Yao et al., "Site-directed Mutagenesis of Herpesvirus Glycoprotein Phosphorylation Sites by Recombination Polymerase Chain Reaction", PCR Methods Appl., 1 205-207 (1992).
Yao, Z., et al., "Varicella-Zoster Virus Glycoprotein gpI/gpIV Receptor: Expression, Complex Formation, and Antigenicity within the Vaccinia Virus-T7 RNA Polymerase Transfection System", J. Virol., 67, 305-314 (1993).

Primary Examiner—Frank C. Eisenschenk
Assistant Examiner—Patrick J. Nolan
Attorney, Agent, or Firm—Mueting, Raasch, Gebhardt & Schwappach, P.A.

[57] ABSTRACT

This invention discloses the incorporation of a peptide QRQYGDVFKGD (SEQ ID NO:1) from glycoprotein gE of Varicella zoster virus into a protein or polypeptide sequence for immunoisolation, immunopurification and immunodetection.

14 Claims, 3 Drawing Sheets

PEPTIDE TAG FOR IMMUNODETECTION AND IMMUNOPURIFICATION

FIELD OF THE INVENTION

This invention relates to the fields of immunodetection and immunopurification and to the incorporation of an immunogenic peptide from a Varicella Zoster Virus glycoprotein into another protein.

BACKGROUND OF THE INVENTION

Inserting a peptide tag into a protein facilitates the characterization of that protein when antibodies to the protein are not available. Recent techniques incorporate a peptide tag into a recombinant protein to aid protein purification or isolation of that protein. Antibodies recognizing the peptide tag facilitate purification and/or isolation. (Brizzard, et al. *BioTechniques* 16:730–735, 1994; Fulton, et al. *Eur. J. Immunol.* 25:2069–2076, 1995; Olah, et al., *Anal. Biochem.* 221:94–102, 1994; Prickett, K. S., et al. *BioTechniques* 7:580–589, 1989). Insertion of the antigenic peptide tag into the protein usually depends upon the availability of unique restriction endonuclease recognition sites within the nucleic acid sequence encoding the protein.

There are two basic strategies used to incorporate an antigenic peptide into a protein. In one method, the nucleic acid sequence encoding the peptide is added to the N-terminus equivalent of nucleic acid that encodes a protein. If the N-terminus contains a signal peptide that is cleaved when the protein enters the endoplasmic reticulum, then a tag inserted at this site will be cleaved during protein maturation. The peptide tag will not be available for mature protein isolation (Waiter, P. et al. *Annu. Rev. Cell Biol.* 10:87–119, 1994).

C-terminal tagging techniques are also available (Olah Z., et al. *Anal. Biochem* 221:94–102, 1994 and Prickett, et al. *BioTechniques 7:580–9, 1989*). These techniques can be used when the addition of the tag to the C-terminus of a protein does not negatively affect the conformation of that protein. There are proteins where N-terminal and C-terminal tagging methods are not useful strategies for incorporating antigenic tags into a protein because, for example, the N-terminus is cleaved during protein maturation or additions to the C-terminus interfere with protein folding.

Reliance on restriction endonuclease recognition sites is not always practical and the addition of a peptide tag to the N-terminus or the C-terminus of a protein may not be useful. There is a need for a strategy to circumvent the limitations created by relying on restriction recognition sites and the limitations created when a tag is merely added to a terminal portion of a protein.

Varicella Zoster Virus (VZV) is a member of the Herpesvirus family. The VZV virion is formed as an icosahedral nucleocapsid surrounded by a lipid envelope containing a number of viral glycoproteins. The VZV envelope glycoproteins include gE, gB, gH, gI, gC and gL. gE is the most abundant protein in the virion envelope (Grose, et al. *Infect. Immun.* 40:381–388, 1983) and is encoded by VZV gene 68. The mature protein is about 98 kDa and is about 623 amino acid residues in length. Glycoprotein gE is the predominant immunogen of VZV and was formerly called gpI or gp98 (Grose, C. *Annu. Rev. Microbiol.* 44:59–80, 1990; Montalvo, E. A., et al. *J. Virol.* 53:761–770, 1985; and Yao, Z., et al. *J. Virol.* 67:305–314, 1993). gE induces neutralizing antibodies and the most antigenic fragment within gE is reported to be between residues 1–134. (Fowler, et al. *Virology* 214:531–540, 1995).

SUMMARY OF THE INVENTION

The present invention identifies a linear antigenic peptide from gE for use as a tag for protein immunopurification and isolation. Recombination polymerase chain reaction (PCR) was used to incorporate the linear antigenic peptide from gE into any desired location within an open reading frame of a protein, independent of restriction endonuclease recognition sites. The combination of the peptide (SEQ ID NO:1) in a protein to produce a chimeric protein and antibody recognizing the peptide is used to immunopurify and/or immunolocalize the chimeric protein.

The nucleic acid encoding the linear amino acid sequence QRQYGDVFKGD (SEQ ID NO:1) was incorporated into nucleic acid encoding a protein to produce a chimeric protein containing a heterologous linear amino acid sequence QRQYGDVFKGD (SEQ ID NO:1). The chimeric protein was recognized by antibody binding to the heterologous amino acid sequence QRQYGDVFKGD (SEQ ID NO:1). In a preferred embodiment the antibody is the monoclonal antibody 3B3.

In another aspect of this invention a method is disclosed for identifying a recombinant chimeric protein comprising the steps of: obtaining a vector capable of directing expression of a protein in a cell wherein the vector comprises a first DNA sequence encoding a protein; incorporating a second DNA sequence encoding the peptide QRQYGDVFKGD (SEQ ID NO:1) in frame into the first DNA sequence; expressing a chimeric protein encoded by the DNA sequence of the incorporating step from a cell; and identifying the chimeric protein, using an antibody binding to the peptide. In one method the cell of the expressing step is prokaryotic and in another the cell of the expressing step is eukaryotic. Preferably the antibody of the identifying step is a monoclonal antibody and in one embodiment the monoclonal antibody is 3B3. In a preferred aspect of this embodiment, the identifying step is immunoaffinity column chromatography, in another the identifying step uses immunofluorescence and in another the identifying step uses flow cytometry.

In another aspect of this invention a kit is disclosed to purify a protein comprising a monoclonal antibody recognizing the peptide fragment QRQYGDVFKGD (SEQ ID NO:1) and a protein including the amino acid sequence QRQYGDVFKGD (SEQ ID NO:1). In one embodiment the monoclonal antibody is 3B3. In another preferred aspect of this invention the kit additionally comprises a vector having at least one restriction endonuclease recognition site positioned to receive a DNA fragment encoding protein and in a preferred embodiment the expression vector contains an antibiotic resistance gene.

In yet another aspect of this invention a method is disclosed for identifying antibody in a sample comprising the steps of: creating a chimeric protein comprising a heterologous peptide fragment QRQYGDVFKGD (SEQ ID NO:1); adhering the chimeric protein to a surface; contacting the chimeric protein with a sample; and detecting antibodies binding to QRQYGDVFKGD (SEQ ID NO:1). In a preferred aspect of this embodiment the adhering step comprises adhering the chimeric protein to a solid surface using an antibody to the chimeric protein and the solid surface is an ELISA multiwell plate. In another embodiment the solid surface is a suspendable particle and in another embodiment the solid surface is a planar membrane.

In yet another aspect of this invention a method is disclosed for identifying a chimeric protein comprising a heterologous a peptide fragment QRQYGDVFKGD (SEQ ID NO:1) comprising the steps of exposing the chimeric protein to a monoclonal antibody recognizing the peptide fragment QRQYGDVFKGD (SEQ ID NO:1); and detecting protein bound to the antibody. In one embodiment the method additionally comprises isolating the chimeric protein. In one embodiment the method employs affinity chromatography and in another the method employs immunofluorescence.

DETAILED DESCRIPTION OF THE INVENTION

Figure 1:
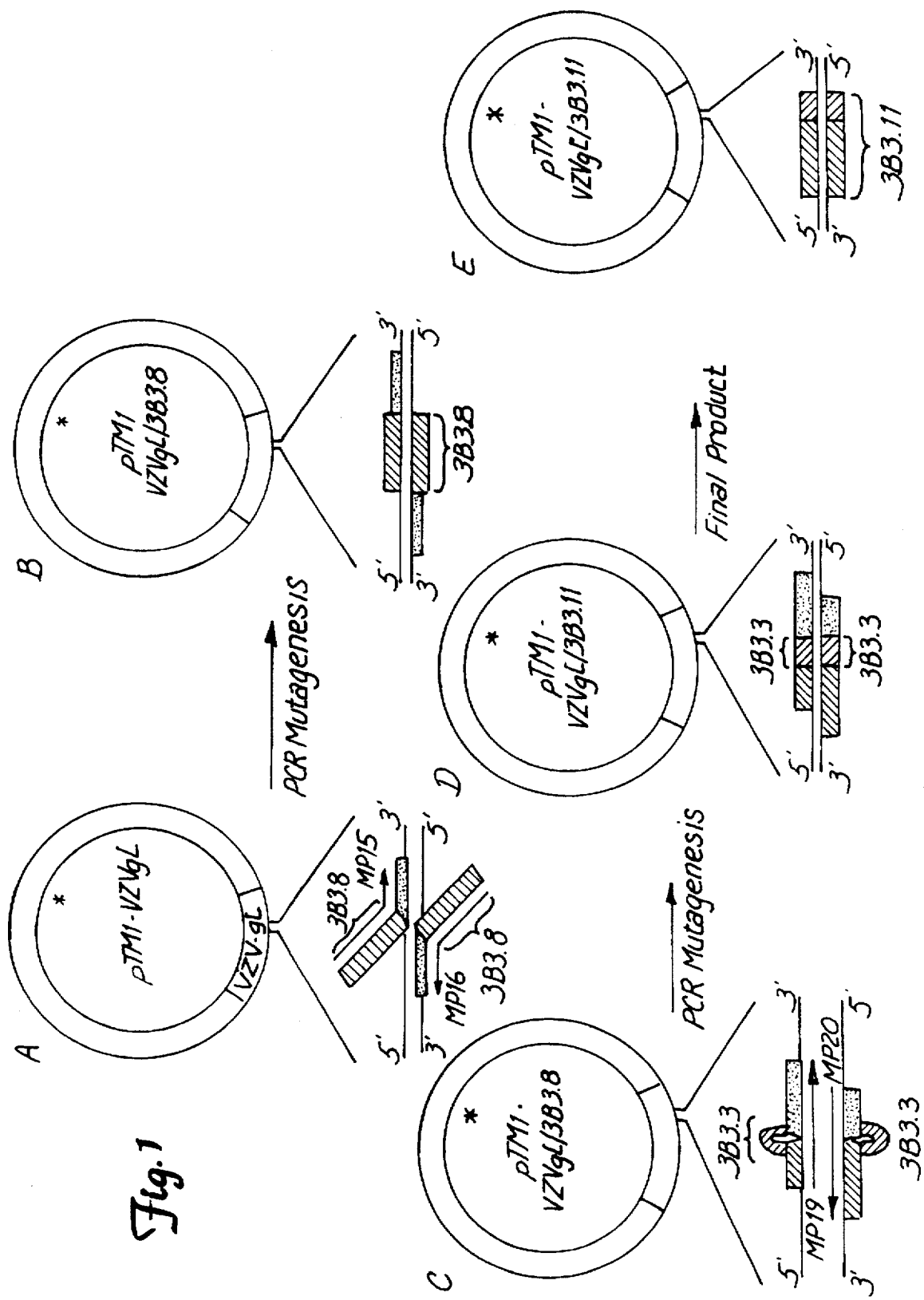
FIG. 1 diagrams a recombination site specific PCR insertional mutagenesis technique employed in this invention. In Panel A mutating primers (MP) MP15 and MP16 were used to insert 24 nucleotides (3B3.8) into the VZV gL gene immediately downstream from codon 21. The darker portions of MP15 and MP16 represent nucleotides that are complementary to the gL template (an overlap of 20 and 21 bp respectively). Panel B represents the resulting pTM1-VZVgL3B3.8 plasmid. Panel C represents PCR insertional mutagenesis where MP19 and MP20 insert 9 nucleotides (3B3.3) into the gL3B3.8 gene immediately downstream from the 3B3.8 insertion. The 3' ends of MP19 and MP20 overlap the gL3B3.8 template by 24 bp each. The 5' ends overlap the gL3B3.8 template by 9 bp and 8 bp respectively. The 3' end of MP20 and the 5' end of MP19 overlap a portion of the 3B3.8 insertion. Panel D and Panel E represent the final incorporation of the 3B3-epitope tag, designated gL3B3.11. An "*" denotes the position within the ampicillin resistance gene where the non-mutating PCR primers (P3 and P4) are located. The primers are listed in Table 2.

The present invention relates to the use of the Varicella Zoster Virus gE peptide fragment QRQYGDVFKGD (SEQ ID NO:1) corresponding to amino acid residues 151–161 from glycoprotein gE and antibodies binding to SEQ ID NO:1 for immunopurification and immunoisolation of proteins other than glycoprotein gE. The peptide sequence was identified using a monoclonal antibody, 3B3, that mapped to 11 residues in the gE ectodomain. Example 1 details the methods used to map antibody MAb 3B3 to a peptide fragment on VZV protein gE.

The peptide, SEQ ID NO:1, or an antigenic fragment thereof, was incorporated into proteins to produce a resulting chimeric protein. The heterologous peptide, SEQ ID NO:1, or an antigenic fragment thereof, functions as an antigenic tag when it is incorporated into a protein or polypeptide. The term "heterologous", as used in this application, indicates that the peptide (SEQ ID NO:1 or an antigenic fragment thereof) of this invention is not part of the native amino acid sequence of the protein into which the peptide fragment of this invention is incorporated. The resulting chimeric protein (i.e., protein plus heterologous peptide) is preferably expressed as a recombinant product in a cell and purification or study of the chimeric protein is facilitated by the use of antibody recognizing the heterologous peptide fragment. The term "chimeric protein" or "chimeric polypeptide" is known in the art and generally refers to a non-naturally occurring protein having a portion or portions of the protein originally derived from a first protein and another portion or portions originally derived from one or more other proteins.

The term "peptide tag" or "antigenic tag" is used to refer to peptides, such as SEQ ID NO:1, that are inserted into a protein. The peptide is preferably inserted inflame into nucleic acid encoding a protein as a piece of nucleic acid encoding the peptide tag. The tag permits the identification, immunopurification and/or immunoisolation of the protein encoded by the nucleic acid.

There are any number of reasons recognized in the art for isolating and/or purifying recombinant protein produced from a cell. For example, recombinant proteins are generated for medical applications for therapies, vaccines, diagnostics and the like. A variety of growth factors, proteins affecting immune system responses, hormones, and the like have been cloned and expressed using large and small scale synthesis techniques. Recombinant proteins are purified for use in food, for bioremediation, and for a variety of industrial applications.

Often antibody to a particular protein is not available or alternatively antibody to a protein does not bind specifically to that protein. In these cases, antibody directed to the protein is not well suited for protein purification, for isolation techniques or for immunolocalization. The incorporation of SEQ ID NO:1 into a protein provides a suitable target for antibody binding. When incorporated into a protein, antibodies recognizing SEQ ID NO:1 can be used to purify or isolate the resulting chimeric protein by any method that employs antibody to isolate or purify a protein. Examples of these methods include, but are not limited to, immunofluorescence including traditional fluorescent microscopy, laser scanning confocal microscopy, immunotagging and identification by electron microscopy, flow cytometry, immunoblotting including Western blotting, immunoprecipitation, and/or immunoaffinity chromatography As a first step for practicing the invention, a chimeric protein is obtained through the addition of the linear amino acid sequence of SEQ ID NO:1, or an antigenic fragment thereof, into a protein. There are a variety of methods for accomplishing this step and the methods employed in this invention permit SEQ ID NO:1 or an antigenic fragment thereof to be added at any location within a nucleic acid sequence encoding protein. Example 3 demonstrates the usefulness of this invention in the isolation of a VZV glycoprotein, gL and Example 4 uses SEQ ID NO:1 to isolate casein kinase II.

The amino acid sequence of SEQ ID NO:1 can be coupled to a protein using a variety of methods including both chemical and recombinant methods. While it is possible to incorporate the linear amino acid sequence of this invention into a protein through chemical coupling; in general, when a protein is prepared for chemical coupling the protein has already been isolated and purified. Therefore, this invention primarily relates to the incorporation of the peptide tag of SEQ ID NO:1 into a recombinant protein through the manipulation of nucleic acid encoding the protein. But, those skilled in the art will recognize that there may be applications where the peptide tag is preferably coupled directly to a protein, glycoprotein, phosphoprotein or lipoprotein using chemical coupling reactions known in the art.

The amino acid sequence of SEQ ID NO:1 can be inserted into any of a variety of locations into a protein using a number of recombinant methods. The DNA sequence encoding SEQ ID NO:1 is preferably CAA CGT CAA TAC GGT GAC GTG TTT AAA GGA GAT (SEQ ID NO:2) and corresponds to VZV gE nucleotides 450–483, as provided in the full length protein sequence published by Davison and Scott. (*J. Gen. Virol.* 67:1759–1816, 1986). In a second embodiment, a particularly preferred nucleic acid sequence encoding SEQ ID NO:1 is CAA AGG CAA TAC GGT GAC GTG TTT AAA GGT GAT (SEQ ID NO:3) and was incorporated into VZV gL as described in Example 2. Other nucleic acid sequences encoding SEQ ID NO:1 are also contemplated in this invention. The wobble position in the third nucleotide of each codon permits some variability in nucleic acid sequence that does not alter the amino acid sequence of SEQ ID NO:1. In addition, it is known that a number of different codons code for the same amino acid. These variations, also encoding the peptide of SEQ ID NO:1, are within the scope of this invention because it is the resulting peptide fragment that provides the immuno-isolation and identification advantages of this invention. The codon variations that result in the same amino acid sequence provided by SEQ ID NO:1 are known in the art and are provided in table form in the text: *Molecular Biology of the Cell* (Alberts, et al. eds. (1994) Garland Publishing, Inc. New York, p. 106 and inside cover).

Earlier methods for incorporating peptide tags into a protein required that the tag be added to either the N-terminus or the C-terminus and these methods often relied on the presence or absence of suitable restriction endonuclease sites. Reliance on existing restriction endonuclease recognition sites is often cumbersome and labor intensive as linker sequences, and the like, are often needed to incorporate the desired nucleic acid sequence encoding the tag into the desired locale. Targeted incorporation of a peptide tag into a recombinant protein cannot be customized for a particular protein because the presence or absence of suitable restriction endonuclease recognition sites is a function of the nucleotide sequence of the protein to which the tag is to be added. In the art, a particular linker sequence is most readily added either at the site of an existing restriction endonuclease recognition site or by blunt end ligation.

Even where suitable restriction endonuclease recognition sites are available, there are reasons why the addition of N-terminal or C-terminal tags are not useful. As discussed in the background section, N-terminal tag addition will not work where the N-terminus includes a leader sequence that is cleaved during protein processing. In certain proteins the C-terminus cannot be altered, as is the case with the VZV glycoprotein gL of Example 1. Duus, et al. discuss strategies for determining whether or not a tag can be incorporated into the C-terminus of a protein (Duus, K. M., et al. *Virology* 210:429–440, 1995). The methods used in this invention permit the tag of this invention to be incorporated anywhere within any protein.

Those skilled in the art could use SEQ ID NO:1 or an antigenic fragment thereof in conventional methods that incorporate the tag of this invention into the N-terminus or the C-terminus. In conventional methods, oligonucleotides are synthesized that include nucleic acid encoding the sequence of SEQ ID NO:1 together with, for example, nucleotides containing restriction endonuclease recognition sites. Oligonucleotides encoding SEQ ID NO:1, or an antigenic fragment thereof, can also be incorporated into the internal regions of the protein using convenient restriction endonuclease recognition sites.

This invention uses PCR methods to incorporate the tag into an internal portion of a protein. There are a number of different methods, all known in the art, that employ PCR and could be used to incorporate nucleic acid encoding SEQ ID NO:1 into a nucleic acid fragment encoding polypeptide or protein. A benefit of PCR is that nucleic acid encoding SEQ ID NO:1 can be incorporated in frame into any location within a protein. Where SEQ ID NO:1 is used as a tag for immunolocalization or immunopurification, the peptide of SEQ ID NO:1 should not interfere with the secondary structure of the target protein. One method to identify candidate insertion sites or to predict whether a particular insertion site will alter secondary structure of the target protein is to use computer modeling to reconstruct the secondary structure of the gene product of interest. Another method to identify candidate insertion sites is to insert nucleic acid encoding SEQ ID NO:1 into a nucleic acid encoding the protein and test the protein for activity. The peptide is inserted at a site that is predicted not to disrupt the conformation of the gene product. Computer programs for modeling are available through a variety of sources and a preferred computer program for this use is available through the Genetics Computer Group (GCG) at the University of Wisconsin (Madison, Wis.).

A preferred method for incorporating the antigenic tag of this invention into a protein or polypeptide is recombination PCR. The use of recombination PCR permits SEQ ID NO:1 to be incorporated into any location in a protein in need of a tag, and this technique is described by Jones, et al. and Yao, et al. (*BioTechniques* 10:1–5, 1991 and PCR *Methods Appl.* 1:205–207, 1992 respectively).

In the technique disclosed by Yao, et al., a nucleic acid sequence encoding protein is first incorporated into a plasmid. Once in the plasmid, PCR is used to mutagenize the protein. As illustrated in FIG. 1 of Yao, et al., four primers are prepared for two separate PCR reactions. Each primer in each pair has a region that overlaps with a primer in the other primer pair. The overlapping regions facilitate recircularization of the plasmid following PCR fragment amplification. One or both of the primers contain the mutation that will be inserted into the protein. The primer pairs are used in separate amplification reactions to produce two amplified fragments. Following amplification of the fragments, the purified fragments are transfected together into cells. The linear fragments anneal inside the cell to form an intact plasmid containing a nucleic acid encoding protein and incorporating the desired mutation. Transformed clones are selected using probes specific for the mutation. Accurate incorporation of the mutation into the nucleic acid is confirmed by DNA sequencing or other techniques recognized in the art.

The Yao, et al. technique was modified in this invention to incorporate SEQ ID NO:1, or an antigenic fragment thereof, into a protein. In this modified technique, a nucleic acid sequence encoding a protein or polypeptide of interest is first incorporated into a plasmid using standard molecular biology techniques. Virtually any plasmid that is suitable to direct expression of the protein can be used and there are a wide variety of commercially available plasmids suitable for protein expression. Since the method is adapted for any plasmid, the gene to be tagged does not need to be subcloned into a pre-specified plasmid in order to perform the mutagenesis procedure.

The recombinant PCR technique of Yao, et al. amplifies the entire plasmid containing the protein as two fragments in two separate PCR reactions. This amplification strategy may not work well for some expression vectors, particularly if the plasmid is quite large. For recombinant PCR methods, where the entire plasmid is recreated as two linear PCR fragments, the total plasmid size with protein insert is preferably no more than 10 kb. In these cases, it is possible to incorporate the protein into a vector better suited for PCK amplification. The mutated protein resulting from the amplification reaction can then be incorporated into a second vector, if desired. Similarly, the vector most useful for protein expression may not be suited for PCK amplification (because of size, for example). In this case the protein can be modified to include the tag while in one plasmid and then incorporated into a second plasmid capable of directing protein expression following incorporation of the tag. Those skilled in the art will also readily recognize that if a smaller plasmid cannot be used to express or to clone the protein and where the combined plasmid plus insert size is greater than about 10 kb, there are other PCK methods available to incorporate a nucleic acid sequence encoding SEQ ID NO:1 into a nucleic acid sequence encoding a protein or polypeptide that do not detract from the use of SEQ ID NO:1 as an antigenic tag.

The mutagenesis method of this invention that was used to incorporate SEQ ID NO:1 into a protein used four oligonucleotide primers. Two PCK primers were designed to include: a) some portion of nucleic acid encoding SEQ ID NO:1; b) a region of homology corresponding to the site where the tag will be incorporated into the protein; and c) optionally a restriction endonuclease recognition site. The other two PCR primers were designed to have homology to a second region in the plasmid that contained a known nucleic acid sequence. For example, a preferred second region is an antibiotic resistance gene positioned at about ⅓ to ½ of the distance around the plasmid from the protein. Primers prepared from the second region were selected based on the known sequence in the antibiotic resistance gene. The nucleotide sequences for a wide variety of antibiotic resistant genes are known in the art and can be found using computer databases such as GenBank, and the like. In the Examples that follow, primers P3 and P4 (see Table 2) were selected based on the sequence of the ampicillin resistance gene. These primers are selected entirely from the ampicillin resistance gene nucleic acid sequence and can be used to amplify other plasmids where the other plasmids contain the ampicillin resistance gene.

The oligonucleotide primers were prepared such that one primer in each pair used in the PCR reaction was from the region of the protein where the tag was to be incorporated and the second primer in each pair was selected from the second region in the plasmid that contained the known nucleic acid sequence, such as an antibiotic resistant gene (see FIG. 1 of Yao, et al., supra). The primers in the second region overlapped with each other and the primers with homology to the protein that incorporated a tag also contained regions of homology to each other to permit overlap. This overlap facilitates annealing of the amplification products to each other and permits plasmid recircularization.

The regions of homology in the primers that were from the protein targeted to incorporate the tag preferably include nucleotides that encode at least a portion of SEQ ID NO:1. Depending on the design of the PCR reactions, preferably one of the primers with homology to the targeted protein contains the entire nucleic acid sequence encoding SEQ ID NO:1. Alternatively each primer with homology to the target protein can contain a portion of the nucleotide sequence encoding SEQ ID NO:1. The primers are designed so that when the amplified fragments that include the overlapping primers overlap and the recircularized plasmid with protein now incorporates the nucleotide sequence encoding SEQ ID NO:1. The primers are also designed so that SEQ ID NO:1 is expressed in-frame in the protein. Those skilled in the art will recognize that alternative primer designs that result in the final incorporation of a nucleic acid sequence encoding SEQ ID NO:1 into the target protein do not detract from this invention. These other primer designs are also within the scope of this invention.

The primers are synthesized as oligonucleotides using standard deoxyoligonucleotide synthesis techniques. Custom oligonucleotide synthesis services are available from companies in a variety of states, including, but not limited to, Amitof Biotech Inc. (Boston, Mass.), Ransomhill Bioscience, Inc. (San Diego, Calif.) or Genset Corp. (LaJolla, Calif.)

The primer pairs were used in two standard PCR amplification reactions to amplify and incorporate nucleic acid encoding SEQ ID NO:1 in frame into nucleic acid encoding all or a portion of the protein. The amplified fragments containing all or a portion of the protein and all or a portion of nucleic acid encoding SEQ ID NO:1 were isolated and purified. In the recombinant PCR technique employed in the Examples and in the method described by Yao, et al. (supra), the two amplified fragments were capable of reannealing to one another by virtue of the overlapping ends in each fragment to recreate the plasmid now having SEQ ID NO:1 incorporated into the target protein (see FIG. 1 of Yao, et al., supra).

The amplified fragments are introduced (i.e., via transfection or transformation, or the like) into a suitable host. Alternatively the nucleic acid encoding the chimeric protein can be introduced into a second plasmid designed or optimized for gene expression in a cell. The ultimate plasmid that is used to express the target protein with tag preferably includes regulatory sequences, including suitable promotors, enhancers, and the like for expressing the gene in bacterial and/or eukaryotic expression systems. In the method of this invention the fragments recircularize inside the transformed or transfected cell. Cells containing protein with tag can be initially selected based on their ability to hybridize to nucleic acid probes derived from the same nucleic acid sequence encoding SEQ ID NO:1 that was incorporated into the nucleic acid sequence encoding protein. Unique restriction endonuclease recognition sites positioned within the primers and now incorporated into the protein can also be used to screen the clones, a technique known in the art. Ultimately, clones are selected based on the ability of the host containing the clone to produce the chimeric protein and the ability of the protein to bind to antibody that recognizes SEQ ID NO:1 or an antigenic fragment thereof.

Example 2 describes the incorporation of nucleic acid encoding SEQ ID NO:1 into glycoprotein gL. gL is a Varicella Zoster Virus glycoprotein but there are currently no monoclonal antibodies available that bind to the protein (Duus, et al. supra and Forghani, B., et al. *Virology* 199:458–462, 1994). gL may contain an N-terminus signal peptide that is cleaved when the protein enters the endoplasmic reticulum and includes secondary structure at the C-terminus that could not be altered. Neither N-terminal nor C-terminal tag addition strategies will work for gL.

The tag provided in SEQ ID NO:1 is used to detect the presence or absence of any recombinant protein where incorporation of the tag into the protein does not block gene expression, alter critical functional domains of the protein that are required for activity, and/or does not substantially disturb the secondary structure of the protein. Conversely, the tag can be used to determine which areas of a protein are necessary for protein expression and which areas of a protein are required for a particular activity of the protein.

The use of the tag to purify, to localize or to study protein function requires the use of an antibody specific for the peptide sequence of SEQ ID NO:1. There are a variety of methods for producing monoclonal antibodies and monoclonal antibody production is well known in the art. Those skilled in the art will be readily able to produce monoclonal antibody to SEQ ID NO:1 and select monoclonal antibodies that specifically bind to a peptide corresponding to SEQ ID NO:1 or to an antigenic fragment thereof. SEQ ID NO:1 is a peptide well suited for integration into protein because the peptide stimulates the production of high affinity antibody and antibody produced using SEQ ID NO:1 or a polypeptide containing SEQ ID NO:1 recognizes the peptide as a linear determinant.

A preferred monoclonal antibody (MAb) used in the Examples is MAb 3B3. This antibody binds specifically and has high affinity for the peptide sequence of SEQ ID NO:1. The hybridoma producing the monoclonal antibody 3B3 is deposited with the American Type Culture Collection (ATCC), 12301 Parklawn Drive, Rockville Md., 20852 as accession number HB-12377, deposited on Jul. 17, 1997 under the terms and conditions of the Budapest Treaty.

Importantly, the specificity of antibody directed to the peptide fragment of this invention is quite high. For example, in the particularly preferred combination of monoclonal antibody 3B3 with SEQ ID NO:1, the antibody binds the epitope even in the presence of 1% sodium dodecyl sulfate. The ability of an antibody to bind under these stringent conditions demonstrates the high affinity of the antibody for its determinant (see Montalvo, et al. *J. Virol.* 53:761–770, 1985). In addition, there is virtually no background noise observed when the antibody is used in immunoprecipitation, immunofluorescence and immunoblotting experiments to detect protein containing the peptide of SEQ ID NO:1.

Methods for producing MAb 3B3 and other monoclonal antibodies directed to SEQ ID NO:1 are described by Grose, et al. (*Inf. Imm.* 40:381–388, 1983). Animals were immunized with a sonicated cell extract of VZV 32 strain virus to identify antibody that neutralized VZV infection. MAb 3B3 neutralized infectivity in the presence of complement and was found to bind specifically to VZV infected cells. Later it was found that the MAb 3B3 bound to gE and Example 1 discloses methods used to map MAb 3B3 to SEQ ID NO:1. Methods for creating monoclonal antibodies from peptides is well known in the art and a review of these tecniques is provided by McCormack et al., ("Advances in Monoclonal Antibody Technology," *Immunochemical Assays and Biosensor Technology for the 1990s*, Nakamura et al., eds., 1992, Am. Soc. Microb.).

SEQ ID NO:1 was added into an interior portion of the VZV protein gL. Antibody recognizing SEQ ID NO:1 was used to identify and detect bacterial colonies expressing the recombinant protein, to isolate the protein by precipitation and to localize the protein within a cell (see Example 3).

Example 3 uses the tag of this invention to identify the cellular location of the chimeric protein in a cell and demonstrates the applicability of the tag for identifying the trafficking of the protein through the cellular milieu. For example, an investigator can use antibodies to SEQ ID NO:1 to test for the presence of a chimeric protein in a cell lysate or a cell fraction. Antibodies to the tag can be used to test for the presence of the chimeric protein in a eukaryotic cell supernatant and methods are known for detecting antibody binding in intact eukaryotic cells, cell sections, fixed cells, or in cell lysates. The antibody can be tagged with a fluorescent dye, with a radiolabel or a heavy metal.

The tag can also be used to detect protein expression in transformed bacteria. The growth media surrounding the bacteria or bacterial lysates can be tested for chimeric protein. Example 2 demonstrates the applicability of the tag to these methods through the use of western dot blots on lysed bacterial colonies.

The tag can also be used as a marker to quantitate the level of gene expression from a cell. Chimeric protein can be quantitated based on western blotting from a dot blot or a gel or through the use of immunoassays, including, but not limited to, ELISA-type assays or radioimmunoassays using antibodies to the tag. There are a variety of immunoassay formats known in the art and antibody to the tag can be bound to sepharose, latex, magnetic beads or the like, to permit protein separation and/or identification. Alternatively, flow cytometry and other immunofluorescent assays can be used to quantitate protein expression of the chimeric protein. These methods are also useful for optimizing an expression system including quantitating protein expression from a particular promoter.

Flow cytometry is useful for detecting cells expressing protein incorporating the tag of this invention. Membrane bound protein can be readily detected by flow cytometry using antibody recognizing SEQ ID NO:1 and methods for flow cytometry are discussed in detail by Litwin, et al. *Virol.* 178:263–272, 1990.

The tag can be incorporated into a protein in various positions along the nucleic acid sequence to determine which portions of a particular protein are necessary for protein expression or necessary for a particular protein function. In one embodiment, PCR insertional mutagenesis is used to incorporate the tag in various locations in a protein. The level of protein expression is assessed following cell in vitro or in vivo translation. The level of protein expression can be correlated with the location of the tag in the protein to optimize protein expression levels, for large scale protein isolation, and/or for protein purification.

The tag also functions as a binding site for column chromatography and protein separation experiments. Antibody to the tag provides a rapid method for identifying, isolating, purifying and quantifying the amount of the chimeric protein in a particular column fraction. Antibody to the tag can be affixed onto sepharose or other beads suitable for column separation. A sample containing the chimeric protein is passed over the column containing the sepharose beads and chimeric protein having the tag is bound to the column. Following a series of washes, the protein is eluted from the column using standard elution techniques. The wash is concentrated or lyophilized, if necessary, to produce a protein concentrate. An example of the use of SEQ ID NO:1 as a tag to facilitate protein purification is provided in Example 3. Methods, including preliminary chromatography methods, and the like, can be used to reduce impurities in a preparation prior to immuno affinity chromatography to obtain chimeric protein with SEQ ID NO:1. A general reference text related to affinity chromatography is *An Introduction to Affinity Chromatography* by C. R. Lowe, (1979) North Holland Publishing Co., Holland and affinity chromatography using VZV protein is described in detail by Friedrichs, et al. (*J. Virol.* 49:992–996, 1984). Methods using antibodies to ease protein isolation and purification are well known in the art.

The tag can also be used to determine protein location within a cell using laser scanning confocal microscopy, traditional immunofluorescence techniques, electron microscopy, and the like. Methods for assessing cell location and surface expression of protein is discussed by Duus, et al. (*Virology* (1995) 210:429–440).

While the invention is discussed as it relates to the incorporation of one peptide equivalent of SEQ ID NO:1, those skilled in the art will recognize that repeat sequences of SEQ ID NO:1 can be incorporated sequentially or simultaneously into one or more locations within a protein. SEQ ID NO:1 and antibody recognizing SEQ ID NO:1 can also be used for large scale recombinant protein isolation and purification. Methods for large scale protein isolation and purification are well known in the art.

Figure 3:
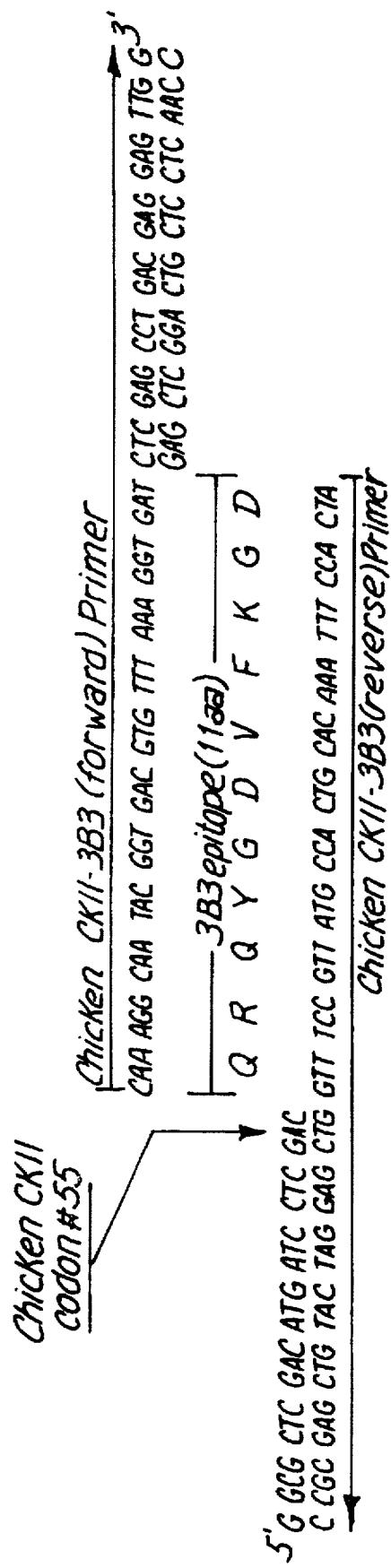
FIG. 3 diagrams the primers, SEQ ID NO:17 and SEQ ID NO:18, and strategy to incorporate nucleic acid encoding SEQ ID NO:1, which is the nucleic acid sequence, SEQ ID NO:3, into nucleic acid encoding casein kinase II.

FIG. 3 and Example 4 detail methods to incorporate nucleic acid encoding SEQ ID NO:1 into another exemplary protein, casein kinase II. The sequence of casein kinase II is provided in GenBank and the gene is isolated from cDNA from a chicken cell expression library using methods known in the art and preferably cloned into pTM1 or another expression vector. The amplification primers P3 (SEQ ID NO:10) and P4 (SEQ ID NO:11) and primers SEQ ID NO:17 and SEQ ID NO:18 are used in paired PCR reactions according to the methods disclosed above and in view of conditions disclosed in Example 2 and Yao, et al. (supra). Amplification of the plasmid as two fragments and transfection into E. coli results in the recircularization of the plasmid and produces a chimeric protein comprising casein kinase II and SEQ ID NO:1. Isolation of protein from E. coli cell lysates is facilitated by the use of antibody to SEQ ID NO:1.

This invention also relates to an immuno assay to identify antibody in a sample. In one embodiment, the antibody that is detected binds to VZV, however, antibody can be detected to any portion of the chimeric protein that is available for antibody binding. In another embodiment, the immunoassay is an ELISA assay. In the ELISA assay, a chimeric protein is prepared to include the heterologous peptide fragment QRQYGDVFKGD (SEQ ID NO:1). The chimeric protein is adhered to a surface either directly by coating the surface with the peptide or indirectly, i.e., by coating an antibody recognizing the chimeric protein on the surface. The surface is preferably a solid surface including suspendable particles, ELISA-type multiwell plates or planar membranes useful for solid-phase chromatography, including, but not limited to, nitrocellulose, Immobulon®, and the like. Standard ELISA procedures are known in the art and following the application of the chimeric protein to a surface and the appropriate washes, the chimeric protein is contacted with a sample, such as sera or other fluid suspected of containing antibody to VZV. In one embodiment, the chimeric protein is the chimeric gL protein of Example 2. Following sample incubation and washing, antibodies are detected in the sample that bind to the chimeric protein. In a preferred detection step, the sample is incubated with anti-human antibody that has been conjugated to a label, including but not limited to fluorescent labels including rhodamine and fluorescein, enzymatic labels including, for example, horseradish peroxidase, radioactive labels and botinylated labels.

Antibody recognizing SEQ ID NO:1 can be used to adhere the chimeric protein to a solid support. Alternatively, antibody recognizing another portion of the chimeric protein can be used to adhere the protein to a solid support. Antibody binding to the chimeric protein in a patient sample includes antibodies binding to SEQ ID NO:1. In one embodiment, the chimeric protein is preferably constructed from a protein that is not typically a protein that would have antibodies in a patient sample that bind to it. In another embodiment, the protein is a VZV protein other than VZV gE and antibody binding to the chimeric protein in the patient sample includes antibody binding to SEQ ID NO:1 and antibody binding to the remaining portion of the chimeric protein. In yet another embodiment, the assay is performed to detect antibody binding to the chimeric protein and antibody to SEQ ID NO:1 is used to adhere the protein to a solid surface.

The invention can be better understood by way of the following examples which are representative of the preferred embodiments thereof, but which are not to be construed as limiting the scope of the invention.

EXAMPLE 1

Mapping of 3B3 fragment

Monoclonal antibody 3B3 was used to isolate a linear epitope on a VZV glycoprotein, gE. MAb 3B3 and rabbit antisera R-60 were produced by methods described by Duus, et al. (supra) and Grose, C. (*Annu. Rev. Microbiol.* 44:59–80, 1990). To identify the location of the peptide fragment recognizing MAb 3B3, the VZV gE gene was excised from the plasmid pTM1-VZV gE (pTM1-ORF 68) by restriction digestion with Sac I and Spe I (see Moss, et al. *Nature* 348:91–92, 1990 and Yao, et al. *J. Virol.* 67:305–314, 1993). Restriction endonucleases were purchased from New England Biolabs (NEB) (Beverly, Mass., USA). pTM1 is available from Dr. Bernard Moss at the National Institutes of Health, Bethesda, Md.

The NovaTope™ System, consisting of the DNase Shotgun™Cleavage Kit, Single dA™ Tailing Kit, pTOPE T-Vector, NovaBlue (DE3) Competent cells, Colony Finder™ Immunoscreening Kit and goat anti-mouse alkaline phosphatase conjugate (Novagen, Madison, Wis., USA), was used to map the MAb 3B3 antibody to a peptide fragment of gE between amino acid residues 131–164.

After separation by agarose gel electrophoresis, the 1.8 kb VZV gE DNA band was cut from an agarose gel and purified with a Geneclean™ Kit (Bio 101, Inc. Vista, Calif., USA). DNase I (diluted 1:133, 1:200, 1:300, 1:450) was used to randomly cleave gE into multiple fragments as part of the DNase Shotgun™ Cleavage Kit. The cleavage products were analyzed on a 2% agarose gel. All DNA bands from 50 bp to 150 bp were cut from the gel and electroeluted with a Gel Eluter (Hoefer Scientific Instruments, San Francisco, Calif., USA). DNA extraction and recovery was performed as described in the Cleavage Kit protocol.

Residue overhang regions on the ds DNA fragments were converted to form blunt ends and a single adenine residue was added to the 3' ends of all fragments with the Single dA™ Tailing Kit; the ds DNA fragments were ligated into the pTOPE T-Vector using the protocol dictated by the Novatope™ System (Novagen). Using the same protocol, the transformation was performed by adding 2.5 µl of the ligation reaction to 50 µl of NovaBlue (DE3) competent cells. The resulting colonies were lifted onto round nitrocellulose filters (Millipore, South San Francisco, Calif., USA) and screened for their ability to bind the 3B3 antibody.

Screening of the filters was carried out as described in the Colony Finder Immunoscreening Kit as part of the Novatope™ system. The system permits expression of cloned fragments from a kit vector in optimized cells supplied by Novagen (supra). The primary antibody was MAb 3B3 and was used at a 1:100 dilution of mouse ascites stock. The secondary antibody was goat anti-mouse alkaline phosphatase conjugate at a 1:10,000 dilution. Four positive bacterial clones were isolated and screened with the PCR primers supplied by the NovaTope™ System (T7 gene 10 Primer and the T7 Termination Primer). The deduced amino acid sequences of the four clones are shown in Table 1. DNA sequencing was performed with an Automated Fluorescent Sequencer at the University of Iowa DNA Core Facility (Iowa City, Iowa) to obtain the gE fragments recognizing monoclonal antibody 3B3.

TABLE 1

Peptides deduced from VZV DNA Sequence

| Clone No. | Sequence | Seq ID No. |
|---|---|---|
| Clone 6B1 (138–158) | LNGDDRHKIVNVDQRQYGDVF | 4 |
| Clone 6B2 (138–161) | LNGDDRHKIVNVDQRQYGDVFKGD | 5 |
| Clone 8B1 (131–161) | GIHVIPTLNGDDRHKIVNVDQRQYGDVFKGD | 6 |
| Clone 8B2 (137–164) | TLNGDDRHKIVNVDQRQYGDVFKGDLNP | 7 |

*DNA sequence of VZV genome from Davison and Scott (J. Gen Virol 67:1759–1816, 1986). Numbers in parentheses represent stretches of the deduced amino acid sequence of VZV gE.

The products of the two shortest clones, 6B1 (21 residues) and 6B2 (24 residues), were screened by chemiluminescent dot blotting. Lysates were prepared using cells containing 6B1 or 6B2 to individually inoculate 4 ml cultures of CircleGrow broth (Bio 101, Inc. Vista, Calif.), which were then incubated at 37° C. overnight in an orbital shaker (225 rpm). The next day, clones 6B1 and 6B2 were induced to produce protein with 5 nM isopropyl-b-6 thiogalactopyranoside (IPTG) (Promega, Madison, Wis., USA). Protein detection was achieved with an Immun-Lite™ II Chemiluminescent Protein Detection System (Bio-Rad Laboratories, Hercules, Calif., USA). Membranes containing the proteins of interest were placed into Immun-Lite Enhancer Solution for 15 min at room temperature. Chemiluminescent developing buffer was prepared with a 25X Substrate Dilution Buffer and the Chemiluminescent Substrate Reagent as directed by the Detection System.

The intensity of the clone 6B1 product was less than that of the clone 6B2 product. Based on the sequences provided in Table 1, the only difference between the 6B1 and 6B2 products was three additional C-terminal amino acid residues in clone 6B2 (159–161; KGD). The remaining residues within 6B1 and 6B2 were identical (138–158). The presence of the three C-terminal residues of 6B2 influenced the expression or presentation of the predicted epitope, therefore, the epitope was in the C-terminal portion within both clones.

EXAMPLE 2

Incorporation of 3B3 Fragment into a Protein

Figure 2:
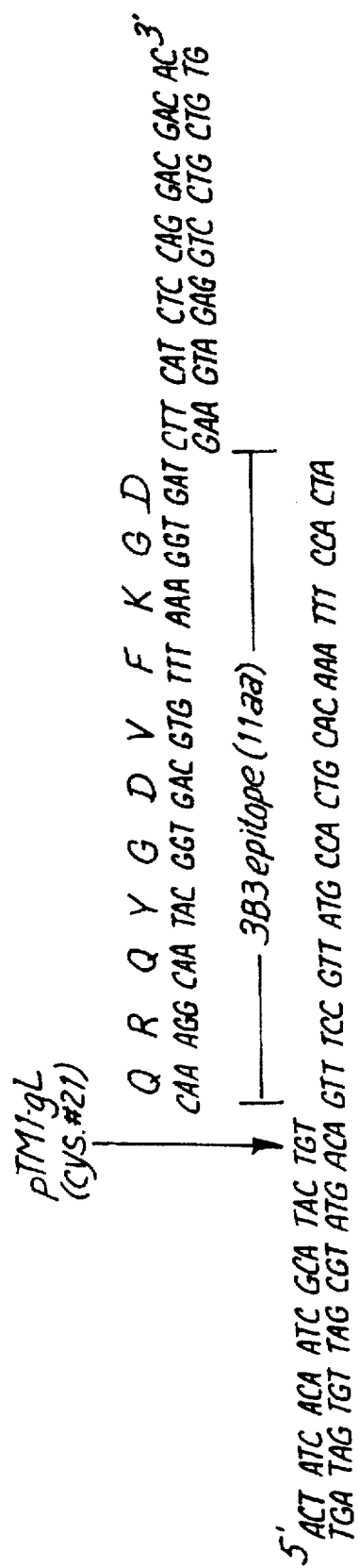
FIG. 2 details the insertion site of amino acid sequence, SEQ ID NO:1, which is the nucleic acid sequence, SEQ ID NO:3, into protein gL.

The last eight amino acid residues of 6B1 (3B3.8; QRQYGDVF, see Table 1 above) were initially inserted into VZV protein gL by a recombination site specific PCR insertional mutagenesis method. (FIG. 1, panel A). The insert was placed downstream from codon 21 of the VZV gL gene, a site known to have little effect on gL function (unpublished, see FIG. 2 for codon 21 location). The sequence of gL is provided as SEQ ID NO:17. The N-terminus sequence before the first methionine (nucleotides 1–3 on SEQ ID NO:17) is ACG TCG TAG TGA AGG GAA AAC ACA AGC GTC ATG when the terminal ATG of this sequence is nucleotides 1–3 of SEQ ID NO:17. The stop codon for the gL protein is located at position 478–480. The primers for PCR mutagenesis were also designed to incorporate a new restriction site, BstNI, into the mutated plasmid for efficient screening of positive clones. The darker portions of MP15 and MP16 (FIG. 1) represent nucleotides complementary to the DNA template (wild-type gL), an overlap of 20 and 21 bp, respectively (Table 2). The asterisk in FIG. 1 denotes the position of the non-mutating PCR primers P3 and P4, which complement an overlapping portion of the ampicillin resistance gene within pTM1 (Table 2, see Duus, et al. supra).

Cloning of the pTM1-VZV gL (pTM I-ORF 60) plasmid was previously described in detail (Duus, et al. *Virology* 210:429–440, 1995). The insert for plasmid pTM1-gL3B3.8 was CAA AGG CAA TAC GGT GAC GTG TTT, nucleic acid sequences 1–24 of SEQ ID NO:3, which was inserted immediately downstream of the cysteine 21 codon of VZV gL.

The plasmid pTM1-VZV gL (6.2 kb) was digested in separate reactions with restriction enzymes Nco I and Spe I and two distinct linear species were obtained. These two linearized forms of pTM1-VZV gL served as templates for PCR mutagenesis, with mutating primers (MP) MP15 and MP16 (Table 2, below). The two non-mutating primers P3 and P4 (Table 2) were located within the ampicillin resistance gene in the pTM1 vector (Duus, et al. supra). Two PCR reactions with paired primers MP15/P4 and MP16/P3 produced two linear products of 2.8 kb and 3.4 kb respectively. The PCR amplification was performed with the Expand™ Long Template PCR System (Boehringer Mannheim, Indianapolis, Ind., USA) as dictated by the Expand protocol, with the following parameters: 94° C. denaturation for 30s, 40° C. annealing for 30s, 68° C. extension for 4 min; after 25 cycles, then 72° C. final extension for 7 min. The newly synthesized DNA strand contains the epitope of interest.

The PCR products were detected by ethidium bromide staining in a 1.2% agarose gel and both PCR products were cleaned with an Ultrafree-MC filter (Millipore). The PCR products were co-transformed into MAX Efficient DH5a™ Competent Cells (Life Technologies, Gaithersberg, Md.) as described by Duus, et al. (supra). When the two DNA strands were recombined in *E. coli*, the new plasmid pTM1-gL-3B3 incorporated the peptide of interest. Eighteen colonies were picked and individually grown in 3 ml aliquots of Circle-Grow broth overnight at 37° C. in an orbital shaker. The plasmid DNA isolated from the colonies were screened by PCR amplification of gL with amplification primers P1 and P2 (Table 2) which flank the gL gene within pTM1-VZV gL. Agarose gel electrophoresis demonstrated that 16 of 18 amplified PCR clones were positive for gL sequences. Five gL positive clones were randomly chosen and digested with BstNl, the unique restriction site created by the mutagenesis, to confirm the presence of the 24 bp inserted sequence. Plasmid DNA from one clone, designated pTM1-gL3B3.8 (FIG. 1B), was isolated and sequenced.

Plasmid purification was carried out with a Qiagen Maxi Kit (Qiagen, Chatsworth, Calif., USA). Sequencing with sequencing primer 2 (SP2) (Table 2) was performed at the University of Iowa DNA Core Facility using standard dideoxy DNA sequencing techniques well known in the art.

TABLE 2

Primers for PCR mutagenesis

| Primer No. | Sequence | SEQ ID NO |
|---|---|---|
| P 1 (rev.) | CAAGCGCCAT GGCATCACAT AAAT | 8 |
| P 2 (for.) | AAACACTAGT CCATGTGCAT GTCCCGC | 9 |

TABLE 2-continued

Primers for PCR mutagenesis

| Primer No. | Sequence | SEQ ID NO |
|---|---|---|
| P 3 (rev.) | AACAGCGGTA AGATCCTTGA G | 10 |
| P 4 (for.) | AAACTCTCAA GGATCTTAC | 11 |
| MP 15 (for.) | CAAAGGCAAT ACGGIGACGT GTTTCTTCAT CTCCAGGACG ACAC | 12 |
| MP 16 (rev.) | AAACACGTCA CCGTATTGCC TTTGACAGTA TGCGATTGTG ATAGT | 13 |
| MP 19 (for.) | GACGTGTTTA AAGGTGATCT TCATCTCCAG GACGACACTC CG | 14 |
| MP 20 (rev.) | AGATGAAGAT CACCTTTAAA CACGTCACCG TATTGCCTTT G | 15 |
| SP 2 (rev.) | GCCAGCCCCT TTAAGGTGA | 16 |

*mutating primers MP15, 16, 19, 20 were synthesized by The Midland Certified Reagent Company (Midland, TX, USA); and non-mutating and sequencing primers were synthesized by the University of Iowa DNA Core Facility (Iowa City, IA, USA)

To determine whether or not the target protein contained the peptide fragment of SEQ ID NO:1, cell lysates containing the gL3B3.8 product were harvested from HeLa cells, then blotted with or precipitated by MAb 3B3 and rabbit antibody R-60 (polyclonal rabbit antisera to gL). The expressed protein was recognized by the gL antiserum R-60, but not by MAb 3B3 (data not shown). Thus, the 3B3 epitope had been incompletely reconstructed in our first set of experiments. These experiments are valuable because they exemplify screening strategies needed to determine whether or not the protein tag is properly incorporated into the protein.

A review of the data in Table 1 suggested that the three additional amino acids (KGD) present in gE peptide clone 6B2 were likely essential for MAb 3B3 recognition. Therefore, an additional PCR insertional mutagenesis experiment was performed with the gL3B3.8 construct. Panel C of FIG. 1 illustrates the recombination PCR strategy with mutating primers MP19 and MP20 (sequences provided in Table 2). This procedure inserted 9 nucleotides (AAA GGT GAT) immediately downstream of codon TTT into pTM1-gL3B3.8 immediately downstream from the 3B3.8 insertion. This plasmid was designated pTM1-gL3B3.11. The 3' ends of MP19 and MP20 each overlapped the template DNA by 24 bp and the 5' ends overlapped the template by 9 and 8 bp, respectively (Table 2). Also, the 5' end of MP19 and the 3' end of MP20 complemented a portion of the 3B3.8 insertion.

In subsequent experiments the plasmid pTM1-VZV gL3B3.8 was digested with restriction enzymes Nco I and Spe I to give two separate linear species, which served as templates for the PCR mutagenesis, with mutating primers MP19 and MP20 and with two non-mutating primers P3 and P4 (Table 2). The 3B3.3 insertional mutagenesis used paired primers MP19/P4 and MP20/P3 which produced two linear products of 2.8 kb and 3.4 kb, respectively. The insert now contained a unique MboI restriction endonuclease recognition site. Recombination site specific PCR insertional mutagenesis of plasmid pTM1-gL3B3.8 (6.2 kb) was performed under the same conditions as the 3B3.8 insertion. Both PCR products were co-transformed into MAX Efficient DH5a™ Competent Cells (Life Technologies, Gaithersberg, Md.). Ten colonies were picked and screened by PCR amplification of gL with primers P1 and P2, as described by Duus, et al. (supra). Agarose gel electrophoresis demonstrated that 8 of 10 amplified PCR clones were positive for gL sequences. Five gL positive clones were randomly chosen and digested with Mbo I. The plasmid DNA of one clone was isolated and sequenced. This plasmid was designated pTM1-gL3B3.11 and contained the 11-codon 3B3-epitope (QRQYGDVFKGD (SEQ ID NO:1)) inserted into the gL gene (FIGS. 1D, E) as confirmed by sequencing.

EXAMPLE 3

Immunoisolation of protein with 3B3 fragment

A. Immunoprecipitation

The gL3B3.11 DNA and wild-type gL DNA were transfected into HeLa cells (ATCC CCL2) (American Type Culture Collection, Rockville, Md., USA) in the presence of 15% Lipofectin® (Life Technologies, Gaithersberg, Md.) as previously described by Duus, et al. (supra). In the VZV-infected cell, gL typically forms a complex with glycoprotein gH, therefore, an antibody that precipitates gL will co-precipitate gH. Immunoprecipitation analyses were carried out with single (gL alone) and dual (gL/gH) transfections.

The cells were labeled for 18 h with 250 µCi/ml of L-[4,5-$^3$H]leucine (Amersham Life Science Inc., Arlington Heights, Ill., USA) in leucine deficient medium (Sigma, St. Louis, Mo., USA) containing 10% FBS (HyClone® Laboratories Inc., Logan, Utah, USA). Lysates of gL-3B3.11 and gH/gL-3B3.11 transfected cells were precipitated with MAb 3B3 and R-60, and then analyzed by 10–18% gradient SDS-PAGE. All precipitates were analyzed in the same gel. The resulting gL-3B3 lysates were subjected to immunoprecipitation with MAb 3B3 or R-60 (rabbit antiserum against gL, see Duus, et al.). The precipitates were analyzed by 10–18% gradient SDS-PAGE under reducing conditions. The dried gels were exposed to radiographic film for 5 to 30 days.

MAb 3B3 recognized the antigenic tag and precipitated gL-3B3 from both lysates. The gL-3B3 chimeric protein had an Mr=21K, which is slightly larger than wild type gL (Mr=20K). This result affirmed the presence of the 11 amino acid antigenic tag within the gL-3B3 protein. In addition, gL-3B3 appeared to be associating normally with gH, as indicated by comparing lysates containing gH and gL-3B3 precipitated by R-60 and MAb 3B3. The negative immunoprecipitation control included T7-vaccinia virus and R-60 antiserum. Wild-type gL could not be precipitated by MAb 3B3.

B. Immunofluorescent detection of the Chimeric Protein

Intracellular localization of the chimeric protein in the cells was investigated by a Bio-Rad 600 laser scanning confocal microscope (Bio-Rad Laboratories). The confocal microscope is especially beneficial due to its ability to optically slice through the cell and define protein localization within individual organelles. To date, tricking of gL has been impossible to study because rabbit antiserum directed to gL also elicited a high background of nonspecific fluorescence. HeLa cells were transfected with gL3B3.11 DNA. Transfected cells were incubated overnight in complete medium (Eagle MEM (Sigma) with 10% FBS, 1.25%: Glutamate, NEAA, Penicillin/Streptomycin). The cell monolayers were fixed with 2% paraformaldehyde, permeabilized with 0.05% Triton, and blocked with 5% normal goat serum. The monolayers were incubated with the primary antibody (MAb 3B3), then with the secondary antibody (goat anti-mouse Ig FITC conjugate, Biosource International, Camarillo, Calif., USA). All samples were analyzed by laser scanning confocal microscopy (Bio-Rad).

Large amounts of fluorescence were observed within cells expressing gL-3B3. The cell nucleus was negatively outlined by abundant perinuclear staining. The positive staining pattern was characteristic of that seen with other viral glycoproteins synthesized within the endoplasmic reticulum. There was no diffuse staining throughout the cytoplasm nor was there any staining of the outer cell membrane. The gL glycoprotein was restricted to the endoplasmic reticulum. This result was unexpected since the major VZV glycoproteins, such as gE, quickly exit the endoplasmic reticulum/Golgi and travel to the outer cell membrane where they are easily detected.

C. Immunoaffinity Column Purification

Monoclonal antibody to SEQ ID NO:1 was prepared from ascites and was concentrated by precipitation with saturated $(NH_4)_2SO_4$ and dialyzed against 0.001M phosphate buffer (pH 7.5). Protein concentration was adjusted to 10 mg/ml and the monoclonal antibody was coupled to CNBr-activated Sepharose by the method of Cuatrecasas (*J. Biol. Chem.* 245:3059–3065, 1970).

The column was packed using standard methods (see Sepharose immunoaffinity techniques provided by Pharmacia, Piscataway, N.J.). Sample was added to the column and allowed to equilibrate. Sample was washed and bound material was eluted with 3M KSCN. Proteins in the final eluate were precipitated with 10% trichloroacetic acid.

For purification of biologically active protein using immunoaffinity chromatography, the monoclonal antibody, here MAb 3B3 was coupled to Sepharose. The protein containing the peptide tag of SEQ ID NO:1 was solubilized in 0.1M sodium citrate buffer (pH 6.0). The protein was exposed to the beads, preferably on a column and the column was thoroughly washed to remove unbound protein. The tagged protein was eluted from the beads with 0.1M glycine HCl buffer (pH 2.5). The eluted fractions were restored to normal pH by the addition of solid Tris. The neutralized samples were concentrated by dialysis against sucrose or polyethylene glycol and further concentrated using an Amicon™ centrifugation-type concentration filter, or the like (Amicon, Beverly, Mass.).

EXAMPLE 4

Incorporation of peptide tag into Casein Kinase II

In a second example, the peptide tag of SEQ ID NO:1 is incorporated in frame into the enzyme casein kinase II. The sequence of casein kinase II is available from the gene sequence database available from the Genetics Computer Group (GCG), University of Wisconsin, Madison, Wis. The nucleotide sequence encoding casein kinase II is incorporated into a plasmid, such as pTM1 vector (Duus, et al. supra.). Following the methods of Example 2, four primers were prepared. Two overlapping primers from a known region of the pTM1 plasmid, such as the gene encoding a protein conferring ampicillin resistance. Exemplary primers from this region include primers P3 (SEQ ID NO:10) and P4 (SEQ ID NO:11). Two overlapping primers were selected to incorporate SEQ ID NO:1 (designated 3B3 epitope on FIG. 3) in frame into the casein kinase protein. A region in the kinase was selected by computer modeling as a region where the insertion of an 11 amino acid peptide would not disturb the secondary conformation of the protein. The forward primer:

5' CAA AGG CAA TAC GGT GAC GTG TTT AAA GGT GAT
CTC GAG CCT GAC GAG GAG TTG G 3' (SEQ ID NO:17)

and the reverse primer:

5' ATC ACC TTT AAA CAC GTC ACC GTA TTG CCT TTG
GTC GAG GAT CAT GTC GAG CGC C 3' (SEQ ID NO:18)

were used. As illustrated in FIG. 3, both the forward and the reverse primers include SEQ ID NO:1 and each primer includes flanking regions in the 3' portion of the primer that correspond to nucleotides from the casein kinase II gene. Nucleic acid encoding SEQ ID NO:1 is incorporated into Chicken CKII at codon 55 as provided in FIG. 3. Amplification of the plasmid including the casein kinase gene in two separate amplification reactions and transfection of the amplified fragments into a suitable host, according to the methods of Example 2 results irk a host expressing a chimeric casein kinase II protein that includes the peptide tag SEQ ID NO:1.

All references, patents, and publications are incorporated by reference in their entirety into this text. Although the invention has been described in the context of particular embodiments, it is intended that the scope of coverage of the patent be limited only by reference to the following claims.

---

What is claimed is:

1. A chimeric protein comprising a protein linked to one or more heterologous peptide tags wherein said peptide tag, or tags, has the amino acid sequence, SEQ ID No. 1, and wherein said chimeric protein binds to antibody to said peptide tag.

2. The chimeric protein of claim 1, wherein the antibody is the monoclonal antibody 3B3.

3. A method for identifying the chimeric protein of claim 1, comprising the steps of: obtaining a vector which directs expression of said chimeric protein, said vector comprising a first DNA sequence encoding a protein and a second DNA sequence encoding said heterologous peptide tag, QRQYGDVFKGD (SEQ ID NO:1) in frame into the first DNA sequence; expressing said chimeric protein in a cell; and identifying said chimeric protein comprising immunodetection with a labeled antibody, wherein said label is a fluorescent dye, radiolabel, enzyme or a heavy metal.

4. The method of claim 3 wherein the labeled antibody binds to the heterologous peptide tag of the chimeric protein.

5. The method of claim 3 wherein the labeled antibody is a secondary antibody which binds a primary antibody, wherein said primary antibody binds to the heterologous peptide tag of the chimeric protein.

6. The method of claim 3 wherein the cell of the expressing step is prokaryotic.

7. The method of claim 3 wherein the cell of the expressing step is eukaryotic.

8. The method of claim 3 wherein the antibody of the identifying step is a monoclonal antibody.

9. The method of claim 8 wherein the antibody of the identifying step is monoclonal antibody 3B3.

10. The method of claim 3 wherein the identifying step uses immunofluorescence.

11. The method of claim 3 wherein the identifying step is a method using flow cytometry.

12. A kit comprising: a monoclonal antibody recognizing the heterologous peptide tag, QRQYGDVFKGD (SEQ ID NO:1) and the chimeric protein of claim 1.

13. The kit of claim 10, wherein the chimeric protein comprises gL.

14. The kit of claim 10, wherein the monoclonal antibody is 3B3.

* * * * *

UNITED STATES PATENT AND TRADEMARK OFFICE
CERTIFICATE OF CORRECTION

PATENT NO.: 5,710,248
DATED: January 20, 1998
INVENTOR(S): Charles F. Grose

It is certified that error appears in the above-identified patent and that said Letters Patent is hereby corrected as shown below:

On the title page,

-in "Other Publication", first A. Vafai document, 2nd line, delete "gpl(ge)" and insert --gpl(gE)--, and delete "12(4)" and insert --12(14)--;

Col. 1, line 3, insert --This invention was made with Government support from the National Institutes of Health, Grant No. NIH AI22795. The Government may have certain rights in this invention.--;

Col. 4, line 7, delete "inflame" and insert --in frame--;

Col. 6, line 11, delete "oft he" and insert --of the--;

Col. 7, line 1, delete "PCK" and insert --PCR--;

Col. 7, line 5, delete "PCK" and insert --PCR--;

UNITED STATES PATENT AND TRADEMARK OFFICE
CERTIFICATE OF CORRECTION

PATENT NO. : 5,710,248
DATED : January 20, 1998
INVENTOR(S) : Charles F. Grose

It is certified that error appears in the above-identified patent and that said Letters Patent is hereby corrected as shown below:

Col. 7, line 13, delete "PCK" and insert --PCR--;

Col. 7, line 20, delete "PCK" and insert --PCR--;

Col. 15, line 10, delete "ACGGIGACGT" and insert --ACGGTGACGT--;

Col. 16, line 52, delete "tricking" and insert --trafficking--; and

Col. 18, line 37, delete "irk a host" and insert --in a host--.

Signed and Sealed this

Fifteenth Day of June, 1999

Attest:

Q. TODD DICKINSON

*Attesting Officer*  Acting Commissioner of Patents and Trademarks

UNITED STATES PATENT AND TRADEMARK OFFICE
CERTIFICATE OF CORRECTION

PATENT NO. : 5,710,248
DATED : January 20, 1998
INVENTOR(S) : Charles F. Grose

It is certified that error appears in the above-identified patent and that said Letters Patent is hereby corrected as shown below:

Column 13,
Lines 58 and 59, delete "The sequence of gL is provided as SEQ ID NO:17.";
Line 61, delete "(nucleotides 1-3 on SEQ ID NO:17)" and insert therefor -- of gL --;
Lines 62-64, delete "when the terminal ATG of this sequence is nucleotides 1-3 of SEQ ID NO:17".

Signed and Sealed this

Eleventh Day of December, 2001

Attest:

NICHOLAS P. GODICI
Attesting Officer
Acting Director of the United States Patent and Trademark Office

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Gln  Arg  Gln  Tyr  Gly  Asp  Val  Phe  Lys  Gly  Asp
    1                 5                                10

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CAACGTCAAT ACGGTGACGT GTTTAAGGA GAT     33

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CAAAGGCAAT ACGGTGACGT GTTTAAGGT GAT     33

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Leu Asn Gly Asp Asp Arg His Lys Ile Val Asn Val Asp Gln Arg Gln
1             5                       10                 15

Tyr Gly Asp Val Phe
            20

( 2 ) INFORMATION FOR SEQ ID NO:5:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Leu Asn Gly Asp Asp Arg His Lys Ile Val Asn Val Asp Gln Arg Gln
1             5                       10                 15

Tyr Gly Asp Val Phe Lys Gly Asp
            20

( 2 ) INFORMATION FOR SEQ ID NO:6:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Gly Ile His Val Ile Pro Thr Leu Asn Gly Asp Asp Arg His Lys Ile
1               5                   10                  15

Val Asn Val Asp Gln Arg Gln Tyr Gly Asp Val Phe Lys Gly Asp
                20              25                  30
```

( 2 ) INFORMATION FOR SEQ ID NO:7:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Thr Leu Asn Gly Asp Asp Arg His Lys Ile Val Asn Val Asp Gln Arg
1               5                   10                  15

Gln Tyr Gly Asp Val Phe Lys Gly Asp Leu Asn Pro
                20              25
```

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CAAGCGCCAT GGCATCACAT AAAT                                                  24

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

AAACACTAGT CCATGTGCAT GTCCCGC                                          27

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AACAGCGGTA AGATCCTTGA G                                                      21

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

AAACTCTCAA GGATCTTAC     19

( 2 ) INFORMATION FOR SEQ ID NO:12:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CAAAGGCAAT ACGGTGACGT GTTTCTTCAT CTCCAGGACG ACAC     44

( 2 ) INFORMATION FOR SEQ ID NO:13:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AAACACGTCA CCGTATTGCC TTTGACAGTA TGCGATTGTG ATAGT     45

( 2 ) INFORMATION FOR SEQ ID NO:14:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GACGTGTTTA AAGGTGATCT TCATCTCCAG GACGACACTC CG     42

( 2 ) INFORMATION FOR SEQ ID NO:15:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

AGATGAAGAT CACCTTTAAA CACGTCACCG TATTGCCTTT G     41

( 2 ) INFORMATION FOR SEQ ID NO:16:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GCCAGCCCCT TTAAGGTGA     19

( 2 ) INFORMATION FOR SEQ ID NO:17:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
CAAAGGCAAT ACGGTGACGT GTTTAAAGGT GATCTCGAGC CTGACGAGGA GTTGG          55
```

( 2 ) INFORMATION FOR SEQ ID NO:18:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

```
ATCACCTTTA AACACGTCAC CGTATTGCCT TTGGTCGAGG ATCATGTCGA GCGCC          55
```